US00PP11169P

United States Patent [19]

Schreurs

[11] Patent Number: Plant 11,169

[45] Date of Patent: Jan. 4, 2000

[54] HYBRID TEA ROSE PLANT NAMED 'SCHOMI'

[75] Inventor: Petrus Nicolaas Johannes Schreurs, De Kwakel, Netherlands

[73] Assignee: Piet Schreurs Holding B.V., De Kwakel, Netherlands

[21] Appl. No.: 08/724,470

[22] Filed: Oct. 1, 1996

[51] Int. Cl.[7] ..... A01H 5/00

[52] U.S. Cl. ..... Plt./137

[58] Field of Search ..... Plt./18, 26, 1, Plt./148, 149, 137, 138

[56] References Cited

U.S. PATENT DOCUMENTS

P.P. 8,619 3/1994 Meilland ..... Plt./18

OTHER PUBLICATIONS

UPOV–ROM, Jan. 1998, Plant Variety Database, GTI Jouve Retrieval Software, citation for 'Schomi'.

UPOV ROM, Plant Variety Database Mar. 1997, 'Naomi' citation. (I).

UPOV ROM, Plant Variety Database Mar. 1997, 'Naomi' citation. (II).

*Primary Examiner*—Howard J. Locker
*Attorney, Agent, or Firm*—Foley & Lardner

[57] ABSTRACT

A new rose plant named 'Schomi' characterized by long stems measuring approximately 90 cm; a distinctive petal color of R.H.S. 55D on the upperside and R.H.S. 38A on the underside; double-type flower with 35–40 petals per flower.

1 Drawing Sheet

The present invention comprises a new and distinct cultivar of rose plant of the Hybrid Tea Rose Class, hereinafter referred to by the cultivar name 'Schomi'.

'Schomi' is a product of a planned breeding program having the objective of creating new rose cultivars which have high yields, longer vase life, longer stems, reduced numbers of thorns and mildew resistance.

'Schomi' was originated from a hybridization made by Petrus N.J. Schreurs in a controlled breeding program in De Kwakel, The Netherlands, in 1988. The female parent was the variety 'Huubda' (Dutch Plant Breeder's Rights No. NL. 9119. The male parent was an unnamed Piet Schreurs De Kwakel B.V. proprietary seedling.

'Schomi' was discovered and selected as one flowering plant within the progeny of the stated parentage by Petrus J.N. Schreurs, in February, 1989, in a controlled environment in De Kwakel, The Netherlands. Asexual reproduction of the new cultivar by budding and cuttings, as performed by Petrus J.N. Schreurs in De Kwakel, The Netherlands, has demonstrated that the combination of characteristics, as herein disclosed for 'Schomi', are firmly fixed through successive generations of asexual reproduction.

'Schomi' has not been observed under all possible environmental conditions. Phenotype may vary significantly with variations in environment, such as temperature, light intensity, and daylength, without any change in genotype.

The following traits have been repeatedly observed and are determined to be basic characteristics of 'Schomi', which in combination, distinguish this rose as a new and distinct cultivar:

1. Double-type flower with 35–40 petals per flower.
2. Petal color on upper side of R.H.S. 55D and on underside of R.H.S. 38A.
3. Length of main stems approximately 90 cm.
4. Length of canes approximately 30 cm.

Of the many commercial cultivars known to the present inventor, the most similar in comparison to 'Schomi' is 'Jacakor'. 'Schomi' has a petal color on the upper side of R.H.S. 55D and on the underside of R.H.S. 38A. 'Schomi' has a bud form that is wide and narrow at the tip. In contrast, 'Jacakor' has a petal color of lilac purple a higher yield, shorter stems, and a bud form that is narrower and less spherical than 'Schomi'.

The parental cultivar 'Huubda' and 'Schomi' are comparable in height and width. However, 'Huubda' has a different pink color, stronger fragrance, and higher yield than 'Schomi'.

The accompanying color photographic drawing shows the typical inflorescence and foliage characteristics of 'Schomi', with colors as nearly true as possible with illustrations of this type.

Sheet 1 is a side view of the plant showing leaves, stems and flowers.

In the following description, color references are made to The Royal Horticultural Society (R.H.S.) Colour Chart. The color values were determined between 10:00 a.m. and 4:00 p.m. under 1.550 J/cma light intensity in De Kwakel, The Netherlands.

Classification:

*Botanical.*—Rosa Hybrida, cv. 'Schomi'.

*Commercial.*—Hybrid Tea Rose.

Plant:

*Habit.*—Bush rose.

*Growth.*—Average vigor.

*Average stem length.*—90 cm.

*Average cane length.*—30 cm.

*Thorns and prickles.*—Young plants have few or no thorns and the number of thorns increases as the plant matures. The thorns measure approximately 0.7 cm in length. The color is yellowish green with a shade of red, R.H.S. 179 A, caused by production of anthocyanin.

*Plant width at maturity.*—Approximately 60 to 70 cm.

*Plant height at maturity.*—Approximately 120 to 130 cm.

*Foliage.*—Shape leaflets: Oval. Leaflet size: Single: 7–8 cm in length and 4.5–6 cm in width. Compound: Most often 3 leaflets form the compound leaf which is about 21 cm in length and about 15 cm in width. Glossiness: Absent. Appearance: Lightly serrated. Color (top side): Medium green (R.H.S. 137A) with dark red shades caused by production of anthocyanin, which appears at the leaf periphery.

Color (bottom side) Light green (R.H.S. 147B). Stipules: Average length is 8 mm. Other foliage characteristics: The leaves curl toward bottom side of the leaves.

Flowers:

*Borne.*—Upright.

*Number of flowers per stem.*—One.

*Buds.*—Peduncle length: Average length is 10–20 cm. Peduncle surface: Smooth with color of green with red shades (R.H.S. 146A). Peduncle strength: Thick and strong. Bud shape: Wide with a tip. Bud size: Average width is 4.5 cm and average length is 5 cm. Bud color: Red, R.H.S. 48 A, variegating to green, R.H.S. 144 B, with a red shade. Receptacle color: Light green with red shades, R.H.S. 48D. Receptacle shape: Wide oval. Receptacle surface: Smooth. Sepal color: Light green, R.H.S. 144 B, variegated with red, R.H.S. 47 B. Sepal appearance: Serrated edges. Sepal surface texture: Pubescence present. Blooms: Size: Diameter of 11–12 cm. Petalage: Number: Double-type (35–40 per flower). Length: 5–6 cm. Texture: Smooth without glossiness. Shape: Broad oval. Hips: Absent. Color: Upperside: White Group R.H.S. 55D. Underside: R.H.S. 38A.

*Fragrance.*—Very weak.

*Reproductive organs.*—Stamens: Average number 140 to 160. Pistils: Average number 150 to 170. Anthers: R.H.S. 10B. Filaments: White (R.H.S. 4D). Pollen: Yellow (R.H.S. 15A). Styles: Yellow (R.H.S. 14C). Stigma: Yellow white. Ovaries: White (R.H.S. 4D).

Other characteristics:

*Disease resistance.*—Average, no significant resistance to any specific pathogen has been observed.

I claim:

1. A new and distinct variety of rose plant named 'Schomi' as illustrated and described.

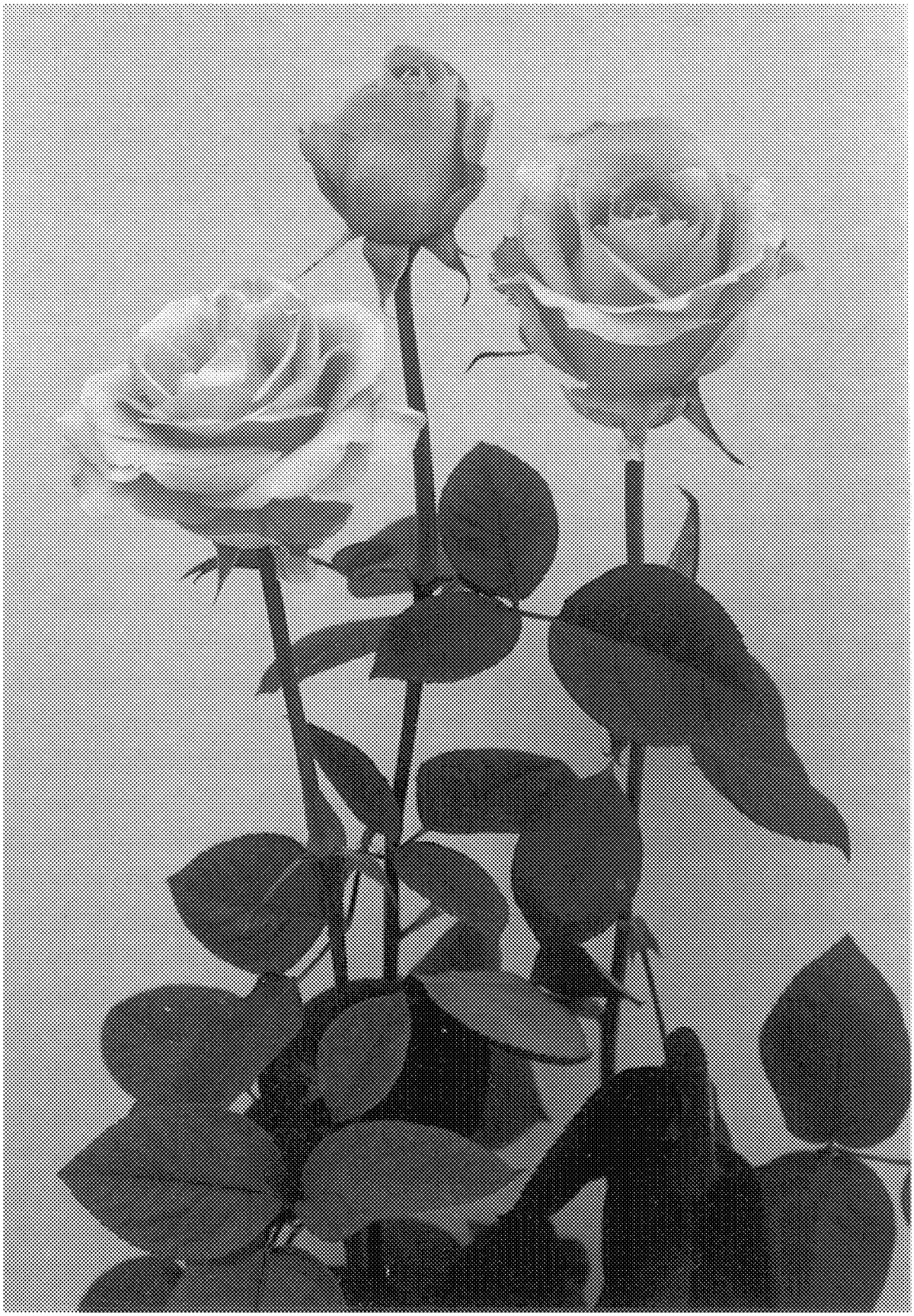

* * * * *